United States Patent
Mostafavi (10) Patent No.: US 10,510,161 B2
(45) Date of Patent: Dec. 17, 2019

(54) PATIENT-MOUNTED OR PATIENT SUPPORT-MOUNTED CAMERA FOR POSITION MONITORING DURING MEDICAL PROCEDURES

(71) Applicant: Varian Medical Systems, Inc., Palo Alto, CA (US)

(72) Inventor: Hassan Mostafavi, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 15/469,385

(22) Filed: Mar. 24, 2017

(65) Prior Publication Data

US 2018/0276846 A1 Sep. 27, 2018

(51) Int. Cl.
| | |
|---|---|
| G06K 9/00 | (2006.01) |
| G06T 7/73 | (2017.01) |
| H04N 7/18 | (2006.01) |
| G06T 7/246 | (2017.01) |
| A61B 90/00 | (2016.01) |
| A61N 5/10 | (2006.01) |

(52) U.S. Cl.
CPC .............. G06T 7/74 (2017.01); A61B 90/39 (2016.02); A61N 5/1049 (2013.01); G06T 7/248 (2017.01); H04N 7/183 (2013.01); *A61B 2090/3937* (2016.02); *A61N 2005/1059* (2013.01); *G06T 2207/30204* (2013.01)

(58) Field of Classification Search
None
See application file for complete search history.

(56) References Cited

U.S. PATENT DOCUMENTS

| 5,742,263 A | 4/1998 | Wang et al. | |
|---|---|---|---|
| 6,081,551 A * | 6/2000 | Etoh | G06T 9/001 |
| | | | 375/240 |
| 2004/0077939 A1* | 4/2004 | Graumann | A61B 6/547 |
| | | | 600/424 |
| 2006/0221397 A1* | 10/2006 | Chung | H04N 1/405 |
| | | | 358/3.03 |
| 2007/0034731 A1* | 2/2007 | Falco | G01B 7/008 |
| | | | 244/3.1 |

(Continued)

FOREIGN PATENT DOCUMENTS

| WO | WO 2015075720 A1 | 5/2015 |
|---|---|---|
| WO | WO 2016055317 A1 | 4/2016 |

*Primary Examiner* — Stephen P Coleman
(74) *Attorney, Agent, or Firm* — Vista IP Law Group, LLP (57) ABSTRACT

An apparatus for use in a medical procedure includes: a camera configured for attachment to a patient, wherein the camera is configured to detect one or more markers outside and away from the patient; and a processing unit configured to receive an input image from the camera, and to process the input image to monitor a position of a target associated with the patient during the medical procedure. An apparatus for use in a medical procedure includes: a camera configured for attachment to a patient support, wherein the camera is configured to detect one or more markers outside and away from the patient support; and a processing unit configured to receive an input image from the camera, and to process the input image to determine a position associated with the patient support during the medical procedure.

26 Claims, 7 Drawing Sheets

(56) References Cited

U.S. PATENT DOCUMENTS

| | | | |
|---|---|---|---|
| 2010/0185102 A1* | 7/2010 | Saar | A61N 5/1049 |
| | | | 600/484 |
| 2013/0129242 A1* | 5/2013 | Lin | G06T 9/004 |
| | | | 382/233 |
| 2013/0237811 A1 | 9/2013 | Mihailescu et al. | |
| 2014/0342331 A1* | 11/2014 | Freeman | G09B 23/288 |
| | | | 434/265 |
| 2016/0344984 A1* | 11/2016 | Fitzgerald | H04N 5/2257 |
| 2017/0004344 A1* | 1/2017 | Nozato | G06K 9/00604 |
| 2017/0263017 A1* | 9/2017 | Wang | G06T 7/73 |

* cited by examiner

PATIENT-MOUNTED OR PATIENT SUPPORT-MOUNTED CAMERA FOR POSITION MONITORING DURING MEDICAL PROCEDURES

FIELD

The field relates to methods and systems for position monitoring during medical procedures, and more particularly, to methods and systems for monitoring a position or a patient or a position of a patient support with respect to its surrounding during medical procedures.

BACKGROUND

Radiation therapy involves medical procedures that selectively expose certain areas of a human body, such as cancerous tumors, to doses of radiation. The purpose of the radiation therapy is to irradiate the targeted biological tissue such that undesirable tissue is destroyed. Radiation has also been-used to obtain image of tissue for diagnostic or treatment purposes.

During delivery of radiation towards a patient, it may be desirable to ensure that a target receiving the radiation remains fixed in position relative to a certain coordinate system. Also, it may be desirable to know the position of a patient support supporting the patient relative to a certain coordinate system.

SUMMARY

An apparatus for use in a medical procedure includes: a camera configured for attachment to a patient, wherein the camera is configured to detect one or more markers outside and away from the patient; and a processing unit configured to receive an input image from the camera, and to process the input image to monitor a position of a target associated with the patient during the medical procedure.

Optionally, the processing unit is configured to receive a reference image from the camera, wherein the reference image or a reference template extracted from the reference image is for comparison with later acquired input images from the camera, one of the later acquired input images being the input image.

Optionally, the processing unit is further configured to extract the reference template from the reference image.

Optionally, the processing unit is configured to compare the input image with a reference image.

Optionally, the processing unit is configured to compare the input image with the reference image by determining a correlation value representing a degree of two-dimensional correlation between the input image and the reference image.

Optionally, the processing unit is configured to compare the input image with the reference image by performing cross-correlation.

Optionally, the processing unit is configured to receive a reference image, extract multiple reference templates from the reference image, and match the reference templates with different parts of the input image.

Optionally, the processing unit is further configured to determine multiple matched positions for the respective reference templates, and compare a pattern of the matched positions with a reference pattern.

Optionally, the processing unit is configured to determine whether the patient has moved based on the comparison of the pattern with the reference pattern.

Optionally, the processing unit is further configured to generate a signal to stop a delivery of an energy beam if a result of the comparison indicates that the patient has moved.

Optionally, the processing unit is further configured to generate one or more control signal(s) to move one or more corresponding components of a medical system if a result of the comparison indicates that the patient has moved.

Optionally, the processing unit is configured to compare the input image with the reference image by performing an image subtraction between the input image and the reference image to obtain a subtracted image.

Optionally, the processing unit is configured to calculate a metric based on an absolute difference of pixel values within a region of interest in a field of view of the camera that corresponds with one of the one or more markers.

Optionally, the metric comprises a variance.

Optionally, the apparatus further includes the one or more markers.

Optionally, one of the one or more markers is mounted at a housing of a treatment machine.

Optionally, one of the one or more markers is mounted to a housing of an imaging machine.

Optionally, one of the one or more markers is mounted to a room.

Optionally, one of the one or more markers comprises a sticker having a geometric pattern.

Optionally, the apparatus further includes a headworn device, wherein the camera is coupled to the headworn device.

Optionally, the headworn device comprises a pair of glasses, a goggle, a helmet, a face-mask, or a headphone.

Optionally, the apparatus further includes a connector for detachably connecting the camera to the patient.

Optionally, the apparatus further includes a structure for carrying the camera, wherein the processing unit is mounted to the structure.

Optionally, the apparatus further includes a structure for carrying the camera, wherein the processing unit is separate from the structure.

Optionally, the apparatus further includes a non-transitory medium for storing the input image and/or a reference image for comparison with the input image.

A method of monitoring a patient during a medical procedure includes: detecting one or more markers outside and away from a patient using a camera that is attached to the patient; receiving an input image from the camera; and processing the input image using a processing unit to monitor a position of a target associated with the patient during the medical procedure.

An apparatus for use in a medical procedure includes: a camera configured for attachment to a patient support, wherein the camera is configured to detect one or more markers outside and away from the patient support; and a processing unit configured to receive an input image from the camera, and to process the input image to determine a position associated with the patient support during the medical procedure.

Optionally, the processing unit is configured to receive a reference image from the camera, wherein the reference image or a reference template extracted from the reference image is for comparison with later acquired input images from the camera, one of the later acquired input images being the input image.

Optionally, the processing unit is further configured to extract the reference template from the reference image.

Optionally, the processing unit is configured to compare the input image with a reference image.

Optionally, the processing unit is configured to compare the input image with the reference image by determining a correlation value representing a degree of two-dimensional correlation between the input image and the reference image.

Optionally, the processing unit is configured to compare the input image with the reference image by performing cross-correlation.

Optionally, the processing unit is configured to receive a reference image, extract multiple reference templates from the reference image, and match the reference templates with different parts of the input image.

Optionally, the processing unit is further configured to determine multiple matched positions for the respective reference templates, and compare a pattern of the matched positions with a reference pattern.

Optionally, the position associated with the patient support comprises a patient support position, and wherein the processing unit is configured to determine the patient support position based on the comparison of the pattern with the reference pattern.

Optionally, the processing unit is configured to compare the input image with the reference image by performing an image subtraction between the input image and the reference image to obtain a subtracted image.

Optionally, the processing unit is configured to calculate a metric based on an absolute difference of pixel values within a region of interest in a field of view of the camera that corresponds with one of the one or more markers.

Optionally, the apparatus further includes the one or more markers.

Optionally, one of the one or more markers is mounted at a housing of a treatment machine.

Optionally, one of the one or more markers is mounted to a housing of an imaging machine.

Optionally, one of the one or more markers is mounted to a room.

Optionally, one of the one or more markers comprises a sticker having a geometric pattern.

Optionally, the apparatus further includes a connector for detachably connecting the camera to the patient support.

A method of determining a position associated with a patient support during a medical procedure, includes: detecting one or more markers outside and away from a patient support using a camera that is attached to the patient support; receiving an input image from the camera; and processing the input image using a processing unit to determine a position associated with the patient support during the medical procedure.

Other and further aspects and features will be evident from reading the following detailed description.

BRIEF DESCRIPTION OF THE DRAWINGS

The drawings illustrate the design and utility of embodiments, in which similar elements are referred to by common reference numerals. In order to better appreciate how advantages and objects are obtained, a more particular description of the embodiments will be described with reference to the accompanying drawings. Understanding that these drawings depict only exemplary embodiments and are not therefore to be considered limiting in the scope of the claimed invention.

DESCRIPTION OF THE EMBODIMENTS

Various embodiments are described hereinafter with reference to the figures. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages of the invention shown. An aspect or an advantage described in conjunction with a particular embodiment is not necessarily limited to that embodiment and can be practiced in any other embodiments even if not so illustrated or if not so explicitly described.

Figure 1:
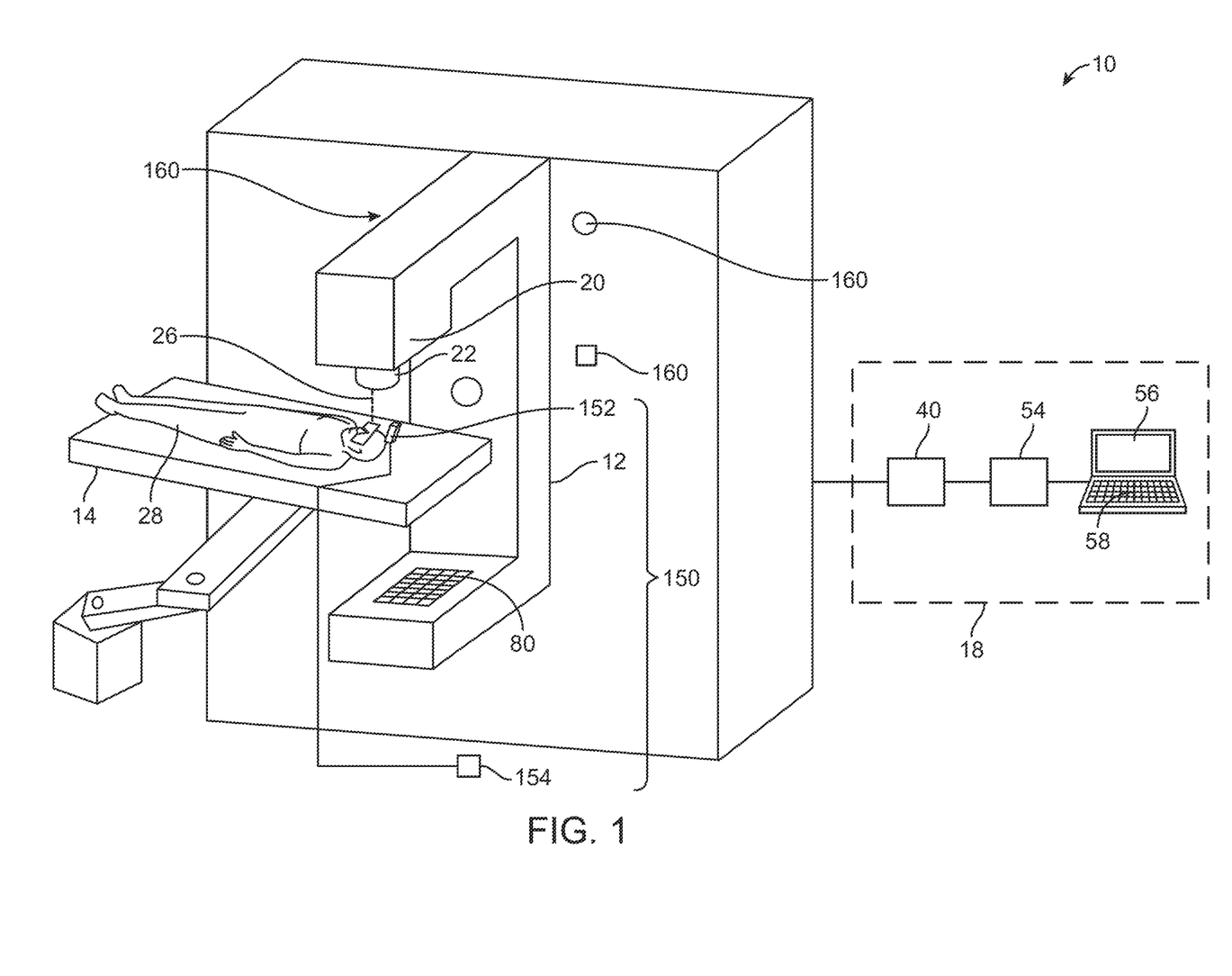
FIG. 1 illustrates a treatment system that includes a camera for attachment to a patient.

FIG. 1 illustrates a medical system 10. The medical system 10 is a treatment system that includes a gantry 12, a patient support 14 for supporting a patient 28, and a control system 18 for controlling an operation of the gantry 12. The gantry 12 is in a form of an arm, but in other embodiments, the gantry 12 may have other forms (such as a ring form, etc.). The system 10 also includes a radiation source 20 that projects a beam 26 of radiation towards a patient 28 while the patient 28 is supported on support 14, and a collimator system 22 for controlling a delivery of the radiation beam 26. The collimator may be configured to adjust a cross sectional shape of the beam 26. The radiation source 20 can be configured to generate a cone beam, a fan beam, or other types of radiation beams in different embodiments.

As shown in the figure, the system 10 also includes an imager 80, located at an operative position relative to the source 20 (e.g., under the support 14). In the illustrated embodiments, the radiation source 20 is a treatment radiation source for providing treatment energy. In such cases, the treatment energy may be used to obtain images. In order to obtain imaging using treatment energies, the imager 80 is configured to generate images in response to radiation having treatment energies (e.g., MV imager). In other embodiments, in addition to being a treatment radiation source, the radiation source 20 can also be a diagnostic radiation source for providing diagnostic energy for imaging purpose. In further embodiments, the system may include the radiation source 20 for providing treatment energy, and one or more other radiation sources for providing diagnostic energy. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. In other embodiments, the radiation source 20 may be configured to generate radiation at other energy ranges.

In the illustrated embodiments, the control system 18 includes a processing unit 54, such as a computer processor, coupled to a control 40. The control system 18 may also include a monitor 56 for displaying data and an input device 58, such as a keyboard or a mouse, for inputting data. The operation of the radiation source 20 and the gantry 12 are controlled by the control 40, which provides power and timing signals to the radiation source 20, and controls a rotational speed and position of the gantry 12, based on signals received from the processor 54. In some cases, the control 40 may also control the collimator system 22 and the position of the patient support 14. Although the control 40 is shown as a separate component from the gantry 12 and the processor 54, in alternative embodiments, the control 40 can be a part of the gantry 12 or the processing unit 54.

As shown in FIG. 1, a position monitoring system 150 is provided for use with the medical system 10. The position monitoring system 150 includes a camera 152 and a processing unit 154 in communication with the camera 152. In some embodiments, the camera 152 and the processing unit 154 may both be mounted to a structure that is for attachment to the patient 28. In other embodiments, the camera 152 may be mounted to a structure that is for attachment to the patient 28, and the processing unit 154 is located away from the structure. For example, the processing unit 154 may be communicatively coupled to the camera 152 or a component at the structure via a cable or a wireless transceiver.

Figure 2A:
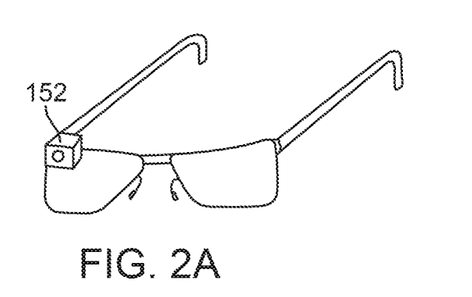
FIG. 2A illustrates a pair of glasses that includes a camera.
Figure 2B:
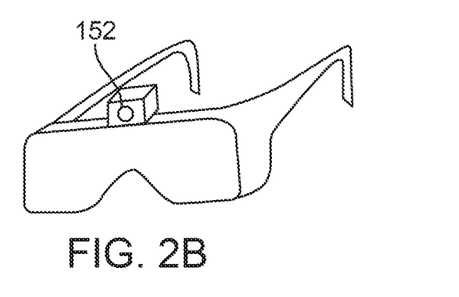
FIG. 2B illustrates a google that includes a camera.
Figure 2C:
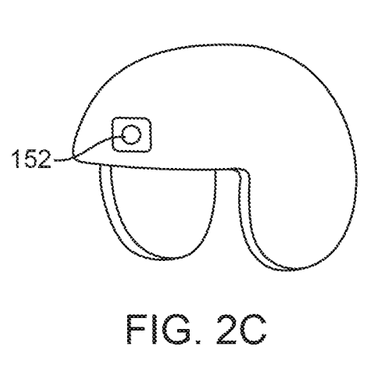
FIG. 2C illustrates a helmet that includes a camera.
Figure 2D:
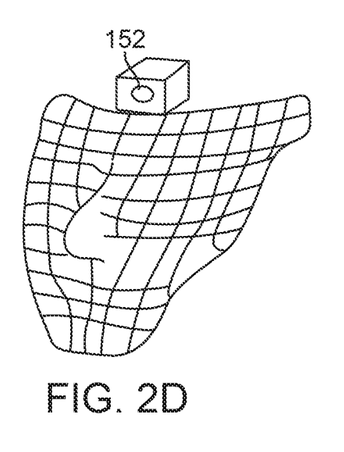
FIG. 2D illustrates a face-mask that includes a camera.
Figure 2E:
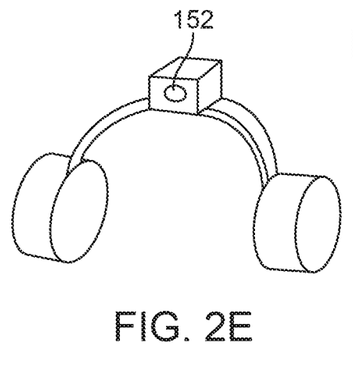
FIG. 2E illustrates a headphone that includes a camera.
Figure 2F:
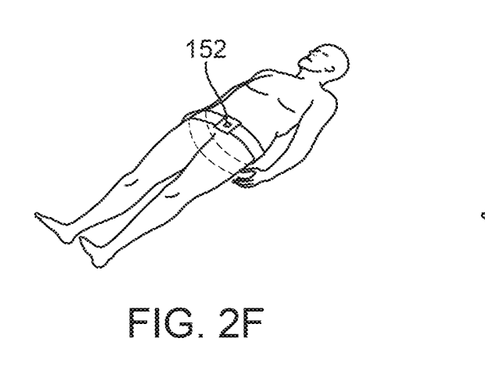
FIG. 2F illustrates a structure for coupling to a torso of a patient that includes a camera.
Figure 2G:
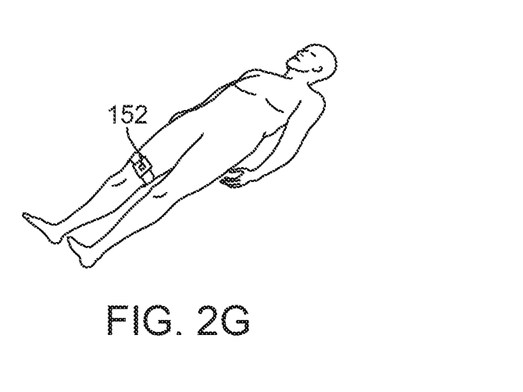
FIG. 2G illustrates a structure for coupling to a limb of a patient that includes a camera.

As discussed, the camera 152 may be mounted to a structure that is for attachment to the patient 28. FIGS. 2A-2G illustrate exemplary structures to which the camera 152 may be secured. FIG. 2A illustrates a pair of glasses that includes the camera 152. FIG. 2B illustrates a goggle that includes the camera 152. FIG. 2C illustrates a helmet that includes the camera 152. FIG. 2D illustrates a face-mask that includes the camera 152. FIG. 2E illustrates a headphone that includes the camera 152. FIG. 2F illustrates a structure for coupling to a torso of the patient 28 that includes the camera 152. The structure may be configured to detachably couple to the patient 28. As shown in the figure, the structure may include a strap for strapping around the torso of the patient 28. FIG. 2G illustrates a structure for coupling to a limb of the patient 28 that includes the camera 152. The structure may be configured to detachably couple to the patient 28. As shown in the figure, the structure may include a strap for strapping around the limb of the patient 28.

Returning to FIG. 1, in the illustrated example shown, the structure carrying the camera 152 is in the form of a pair of glasses. During use, the camera 152 is attached to the patient 28. Also, one or more markers are attached to the system 10. In the illustrated example, there are three markers 160 attached to different parts of the system 10. As shown in the figure, the markers 160 are attached to different parts of a housing of the system 10. In other embodiments, the markers 160 may be attached to other components of the system 10. In some embodiments, the markers 160 are attached to components of the system 10 that are expected to remain fixed in position relative to the target associated with the patient 28 during the medical procedure. Each marker 160 may comprise a sticker for attachment to the system 10. The camera 152 is then used to capture images of the markers 160 for the purpose of position monitoring. In some embodiments, each marker 160 may have a geometric pattern for allowing the processing unit 154 processing the input image from the camera 152 to identify the marker 160. For example, a marker 160 may have a triangular shape, an elliptical shape, a circular shape, a square shape, or any of other shapes. In other embodiments, instead of being attached to the system 10, one or more of the markers 160 may be attached to a room (e.g., a ceiling, a wall, a floor, etc.). In some cases, the markers 160 may be part of an apparatus that also includes the camera 152 and the processing unit 154.

Figure 3:
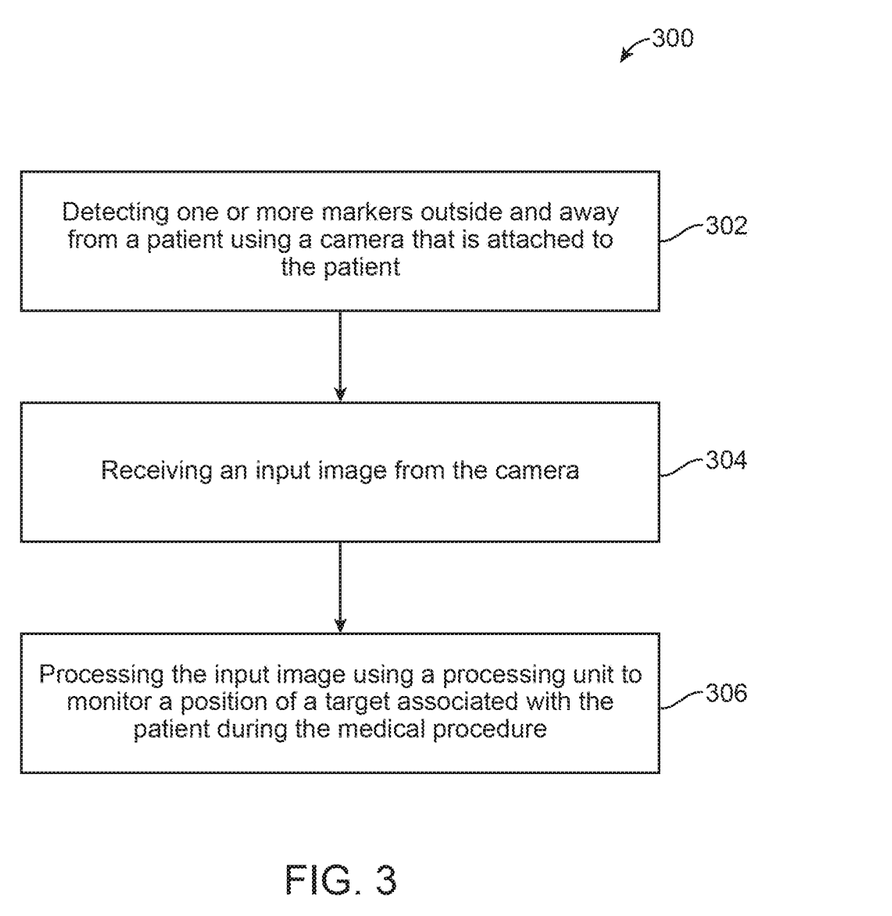
FIG. 3 illustrates a method of position monitoring.

FIG. 3 illustrates a method 300 of position monitoring during a medical procedure. As used in this specification, the term "position" may refer to a location (e.g., X-coordinate, Y-coordinate, Z-coordinate, or any combination of the foregoing) and/or an orientation (e.g., a first angle about a first axis, a second angle about a second axis, a third angle about a third axis, or any combination of the foregoing). Also, as used in this specification, the term "monitoring" or similar terms may refer to determining whether there is movement or not, determining a position, or both. The medical procedure may be a treatment procedure in which energy beam is delivered to the patient 28 to treat the patient 28, and/or an imaging procedure in which imaging beam is delivered to image the patient 28.

Referring to the figure, first, one or more markers 160 outside and away from the patient 28 are detected using the camera 152 that is attached to the patient 28 (item 302). Next, an input image from the camera 152 is received by the processing unit 154 (item 304). Next, the input image is processed using the processing unit 154 to monitor a position of a target associated with the patient 28 during the medical procedure (item 306). In some embodiments, items 302, 304, 306 are repeated during the medical procedure in order to continuously monitor the position of the target. For example, the camera 152 may be configured to repeatedly generate real-time input images, and the processing unit 154 processes these input images in real-time (e.g., within a short time after the image is generated, such as within 1 second, and more preferably within 0.5 second, and more preferably within 0.1 second) to monitor the position of the target associated with the patient.

In some embodiments, in item 306, the processing of the input image may involve use of a reference image provided by the camera 152. In particular, during a setup procedure, the processing unit 154 may be configured to receive a reference image from the camera 152. Then during the medical procedure, the camera 152 captures and provides additional images, and the processing unit 154 then compares the reference image with the later acquired input images from the camera 152. In some cases, the later acquired input images may be real-time input images that are captured by the camera 152 during the medical procedure. In one implementation, the processing unit 154 may include an image comparator for comparing input image(s) from the camera 152 with the reference image.

In some embodiments, the reference image and the real-time input images may be generated in the same session. In other embodiments, the reference image may be generated in a different session from that of the real-time input images. In such cases, the camera used to generate real-time input images should be setup such that the viewing direction and distance are the same as the setup used to generate the reference image.

Also, in some embodiments, after the reference image is received by the processing unit 154 from the camera 152, the processing unit 154 may process the reference image to obtain a reference template. Such may be accomplished using a template generator in the processing unit 154. For example, the template generator of the processing unit 154 may perform image filtering, image enhancement, feature extraction, etc., or any combination of the foregoing, on the reference image to obtain the reference template. In one implementation, the processing unit 154 may process the reference image to obtain the reference template such that the reference template includes only images of the respective markers 160. In another implementation, the reference template may include images of the markers 160 that have been enhanced relative to the background image. The reference template may be smaller in size than that of the reference image. For example, the reference template may be a subset of a two-dimensional extent of the reference image. In other embodiments, the reference template may be equal in size to that of the reference image. In further embodiments, instead of obtaining one reference template from the reference image, the processing unit 154 may obtain multiple reference templates from the reference image. For example, there may be one reference template for each of the markers 160 detected by the camera 152. In any of the embodiments described herein, a reference template itself may be considered as a reference image. Accordingly, as used in this specification, the term "reference image" may refer to the original image provided by the camera 152, or a processed image resulted from processing the original image from the camera 152. The processed image may include an image of a marker 160, or images of multiple markers 160. Also, the processed image may be smaller or equal in size compared to that of the original image.

In some embodiments, in item 306, the image comparator in the processing unit 154 is configured to compare the input image with a reference image. For example, the processing unit 154 may be configured to compare the input image with the reference image by determining a correlation value representing a degree of two-dimensional correlation between the input image and the reference image. In some embodiments, the processing unit 154 may be configured to compare the input image with the reference image by performing cross-correlation. It should be noted that the term "cross-correlation", as used in this specification, refers to determining a plurality of correlations at different offsets over a search region with respect to two images (e.g., the input image and the reference image). Such may be accomplished using template matching technique. In one implementation, the processing unit 154 may compare a correlation value (representing a degree of match between the input image and the reference image) with a threshold. If the correlation value is higher than the threshold, then the processing unit 154 may determine that the patterns match each other. In one implementation, a correlation value of 1.0 represents a perfect match. In such cases, the threshold may be 0.7 or higher, or more preferably 0.8 or higher, or more preferably 0.9 or higher.

In some cases, if the reference image includes images of multiple markers 160, then the comparison of the reference image with the input image may involve comparing the pattern of the images of the markers 160 in the reference image with the pattern of the images of the markers 160 in the input image. If the patterns match, then the processing unit 154 may determine that the patient 28 has not moved. On the other hand, if the patterns do not match, then the processing unit 154 may determine that the patient 28 has moved.

Figure 4:
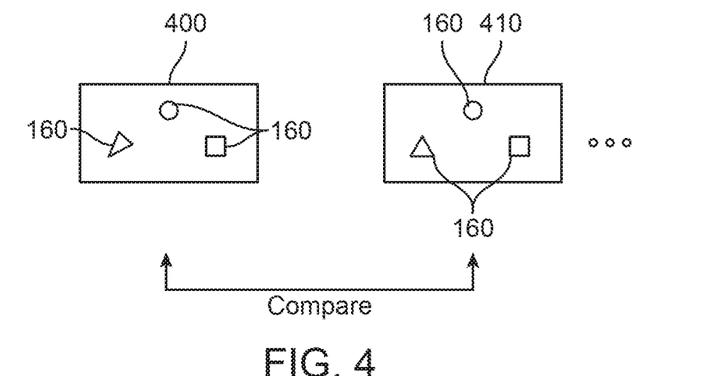
FIG. 4 illustrates a processing of a reference image with an input image.

FIG. 4 illustrates a processing of a reference image 400 with an input image 410. As shown in the figure, the pattern of the images of the markers 160 in the input image 410 is compared with the pattern of the images of the markers 160 in the reference image 400. If the patterns match each other, then the processing unit 154 may determine that there is no patient movement. In one implementation, the processing unit 154 may compare a correlation value (representing a degree of match between the two patterns) with a threshold. If the correlation value is higher than the threshold, then the processing unit 154 may determine that the patterns match each other. In one implementation, a correlation value of 1.0 represents a perfect match. In such cases, the threshold may be 0.7 or higher, or more preferably 0.8 or higher, or more preferably 0.9 or higher.

Figure 5:
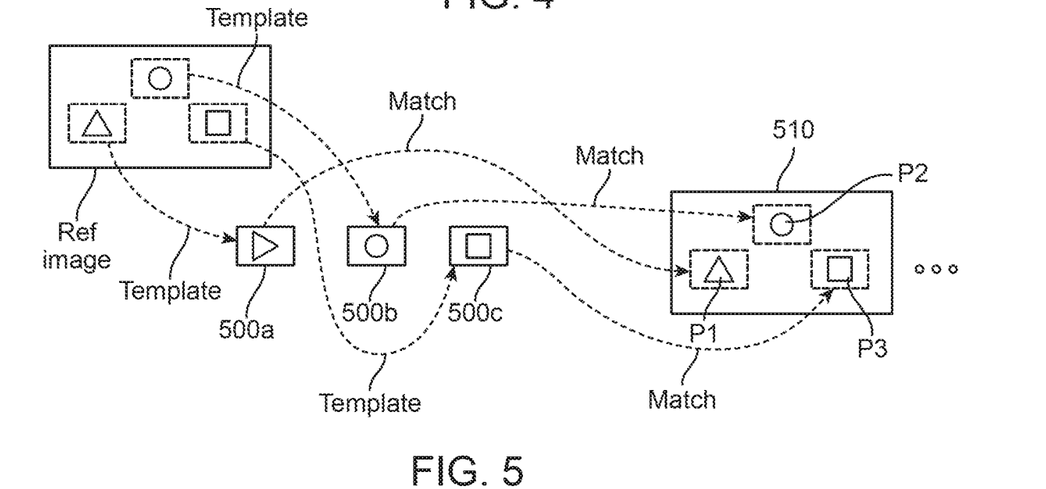
FIG. 5 illustrates template matching between reference templates and different parts of an input image.

In other cases, the reference image may be used by the processing unit 154 to derive multiple reference templates that correspond with respective markers 160. The reference templates may be determined using a template generator in the processing unit 154. In such cases, in item 306, the processing unit 154 may match the reference templates with different parts of the input image. For example, the processing unit 154 may determine respective correlation values representing respective degrees of match between the reference templates and respective parts of the input image. In some cases, the processing unit 154 may perform cross-correlation between the reference templates with respective portions of the input image. FIG. 5 illustrates template matching between the reference templates 500a-500c and different parts (search regions) of the input image 510. As shown in the figure, different parts of the input image 510 are matched with respective reference templates 500a-500c. In one implementation, each of the reference templates 500a-500c is unique, resulting in a one-to-one correspondence with respective parts of the input image 510. For example, the three markers 160 may have different respective shapes, thereby resulting in three different corresponding reference templates.

In some cases, the processing unit 154 performs an image comparison to determine which portion of the input image best matches with each of the reference templates. Known techniques for performing image analysis, such as pattern matching, may be used. For example, if a reference template contains an image formed by 50×50 pixels, the processing unit 154 may perform a spatial analysis to determine a region (having 50×50 pixels) within the input image that best matches the reference template. If there are three markers 160, then there will be three reference templates for matching three corresponding parts of the input image. The processing unit 154 then computes values representative degrees of match between the reference templates and different corresponding parts in the input image. The position of the image within the input fluoroscopic image that best matches the registered template may be stored in a computer-readable medium for later use. In one embodiment, each cross correlation between the input image and a reference template results in a 2D correlation function with a correlation peak. In each correlation function, the location of the peak indicates the position of the marker 160 in the input image that best matches the reference template, and the value of the peak indicates a degree of match between the portion of the input image and the reference template.

Figure 6:
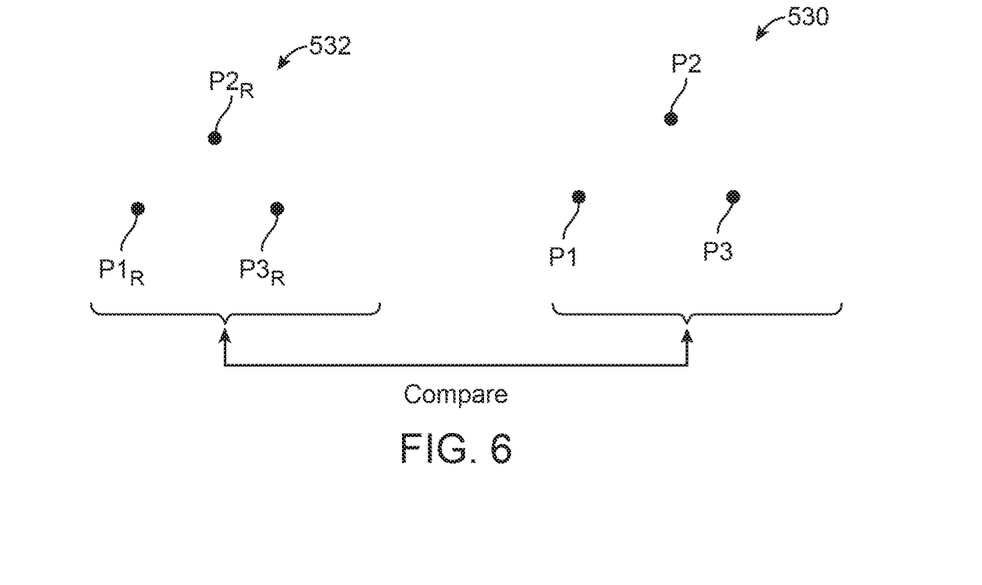
FIG. 6 illustrates a comparison of a pattern of images of markers as they appear in an input image with a reference pattern.

The processing unit 154 may also be configured to determine multiple matched positions for the respective reference templates, and compare a pattern of the matched positions with a reference pattern. FIG. 6 illustrates a comparison of the pattern 530 of the positions P1, P2, P3 of the markers 160 as they appear in the input image 510 with reference pattern 532 of the positions $P1_R$, $P2_R$, $P3_R$ of the markers 160 as they appear in the reference image. The pattern of the images of the markers 160 may be determined based on the matched positions of the reference templates 500. The processing unit 154 may also determine whether the patient 28 has moved based on the comparison of the pattern with the reference pattern. For example, if the pattern from the input image matches the reference pattern, and if the pattern from the input image has not shifted with respect to the reference pattern, the processing unit 154 may then determine that the patient 28 has not moved. On the other hand, if the pattern from the input image does not match the reference pattern, the processing unit 154 may then determine that the patient 28 has moved.

In some embodiments, the method 300 may optionally further include generating a signal to stop a delivery of the radiation beam if a result of the comparison between the input image and the reference image indicates that the patient 28 has moved. For example, the processing unit 154 may include a signal generator configured to generate a signal to stop a delivery of the radiation beam if a result of the comparison indicates that the patient 28 has moved.

In other embodiments, instead of performing cross-correlation between the input image and the reference image (e.g., between the entire input image and the entire reference image, or between a part of the input image and a part of the reference image), the processing unit 154 may include a comparator configured to compare the input image with the reference image by performing an image subtraction between the input image and the reference image to obtain a subtracted image.

In one implementation of the image subtraction described above, a real-time input image $I_n$ is generated using the camera 152. The current input image $I_n$ is subtracted from the reference image RI to obtain a composite image $CI_n$ (i.e., $CI_n=RI-I_n$). In some embodiments, the entire input image $I_n$ may be used. In other embodiments, a region of interest (ROI) in the input image may be used. In such case, the input image $I_n$ is subtracted from the reference image RI over the ROI. In other words, a portion of the input image $I_n$ having the same position as the ROI in the reference image RI is selected and subtracted from the reference image in the ROI to obtain the composite image $CI_n$. The composite image $CI_n$ is then analyzed to determine whether there has been target movement. If there has been target object movement, the pixels in the composite image $CI_n$ should have an increase in contrast. The target may be considered to have moved if the contrast increase is above a certain prescribed threshold. The next real-time input image is then generated and the previously described process is repeated until the end of the medical procedure is reached.

In some cases, the processing unit 154 includes a metric generator configured to calculate a metric based on a difference of pixel values (i.e., values of pixels of the subtracted image) within a region of interest in a field of view of the camera 152 that corresponds with one of the one or more markers. For example, the metric may be a variance.

In some embodiments, instead of, or in addition to, detecting movement of the patient 28, the processing unit 154 may also be configured to determine a position of the patient 28 (after the patient 28 has moved) based on an input image from the camera 152. In one implementation, the processing unit 154 may include a position determination module configured to calculate a new position of the patient 28 based on a pattern of the images of the markers 160 as they appear in an input image. For example, in some embodiments, the processing unit 154 may be configured to use a single-image position and rotation estimation (e.g., six degrees of freedom) to determine the position of the patient 28.

In one implementation, the positions of the markers 160 may be surveyed relative to a machine or room reference coordinate system. By tracking individual markers in the camera's field of view, the processing unit 154 can track the six degrees of freedom of the body part (to which the camera 152 is mounted) relative to the machine or room reference coordinate system.

In some embodiments, the method 300 may optionally further include moving one or more components of the medical system 10 based on a result of the comparison between the input image and the reference image. In one implementation, if the result of the comparison indicates that the patient 28 has moved, the processing unit 154 may then determine the moved position of the patient 28. Based on the moved position, and the previous position, of the patient 28, the processing unit 154 may then determine a direction of the movement, and an amount of the movement. The processing unit 154 may also determine which component(s) of the system 10 move, and an amount of the movement for the component(s) in order to compensate for the movement of the patient 28. The processing unit 154 may include a signal generator configured to generate one or more control signal(s) to move one or more corresponding components of the medical system 10. The movement of the components of the medical system 10 may be performed so that the radiation beam is still delivered at an intended target of the patient 28 despite the movement of the patient 28. For example, the movement of the component(s) may involve moving a gantry, moving a radiation source, moving leaves of a collimator, moving the patient support 14, or any combination of the foregoing, to track the movement of the patient 28.

In other embodiments, instead of moving the component(s) to track the movement of the patient 28, the component(s) of the medical system 10 may be moved to default starting position to allow an operator to reposition the patient 28, or may be moved to allow the patient 28 to be unloaded from the patient support 14.

In any of the embodiments described herein, the position monitoring system 150 may further include a non-transitory medium for storing the input image(s) and/or the reference image (or reference templates derived from the reference image).

In the above embodiments, the position monitoring system 150 was described with reference to the camera 152 being attached to the patient's head. Such technique may be useful when treating a target region in the patient's head. During use, the camera 152 continuously detects images of the markers 160 next to the patient 28, and the processing unit 154 performs comparison between a reference image and the real-time input images from the camera 152. If the patient 28 moves his head, the processing unit 154 will be able to detect such movement based on a result of the comparison. The system 10 may then be operated to cease delivery of the treatment beam.

In other embodiments, the camera 152 may be attached to another part of the patient 28. For example, the camera 152 may be attached to a torso of the patient 28. During treatment, the patient 28 may be instructed to perform breath-hold. After the breath-hold is performed, the camera 152 at the torso may capture and provide a reference image for later comparison. The system 10 is then controlled to deliver treatment beam towards a target region in the torso of the patient 28. While the treatment beam is being delivered, the camera 152 continuously view the markers 160 next to the patient 28, and provides real-time input images for processing by the processing unit 154. The processing unit 154 compares each of the input images with the reference image to determine if the torso has moved since the patient 28 has performed the breath-hold. If the patient 28 moves the torso during the delivery of the treatment beam, the processing unit 154 may then generate a control signal to stop the delivery of the treatment beam.

It should be noted that in this specification, when the camera 152 is being described as "attached" to the patient 28, the camera 152 or a structure carrying the camera 152 may be directly attached to an anatomical part (e.g., a skin) of the patient 28, or the camera 152 or a structure carrying the camera 152 may be indirectly attached to the patient 28 (e.g., through a blanket, a clothing, a cover, etc., that is covering at least a part of the patient 28).

The patient-mounted camera configuration described above is advantageous over an alternative solution in which a room-mounted or machine-mounted camera is used to view the patient. Motion sensitivity and accuracy of a camera-based monitoring system are related to a number of camera pixels that encompass the target being monitored. In the case of room or machine mounted cameras, there is a trade-off between two competing goas: (1) the desire to cover an area several times larger than a target (e.g., a body part) being monitored in order to accommodate motion of the target within the fixed camera's field of view, and (2) a desire to cover the target with a large enough number of pixels in order to maximize detection and localization accuracy. Because of limited resolution of a camera, this trade-off may lead to compromising detection accuracy, as well as the range of target positions that are covered by the camera. The above-described patient-mounted camera configuration may overcome this problem because the markers affixed to the machine and/or the room may be spread out in such a way that for all expected camera orientations, they can be covered by many of the available pixels in the camera's field of view. This also results in high localization accuracy.

Another advantage of the embodiments described herein is high sensitivity in detecting the rotation of the body part to which the camera is affixed. For example, in radiosurgery, almost all movement of a radiotherapy target inside a patient's head is due to rotation of the head. A 0.1 degree (0.0017 radians) rotation around the longitudinal axis may result in around 0.17 mm displacement at the patient face level (assuming a 10 cm radius of the head around the longitudinal axis). A camera mounted at 2 meters away from the patient (e.g. on a ceiling mount) may have a resolution no more than 0.5 mm per pixel on the patient face surface. Therefore, a 0.1 degree rotation results in a ~0.33 pixel displacement of a face landmark in the camera image. On the other hand if the same camera is affixed to the patient head looking at a marker 2 meters away, the same 0.1 degree rotation will result in 0.0017×2000/0.5=6.8 pixel displacement of the marker in the camera image. That means mounting the camera to the patient would result in much higher sensitivity and accuracy in the detection of rotation.

Figure 7:
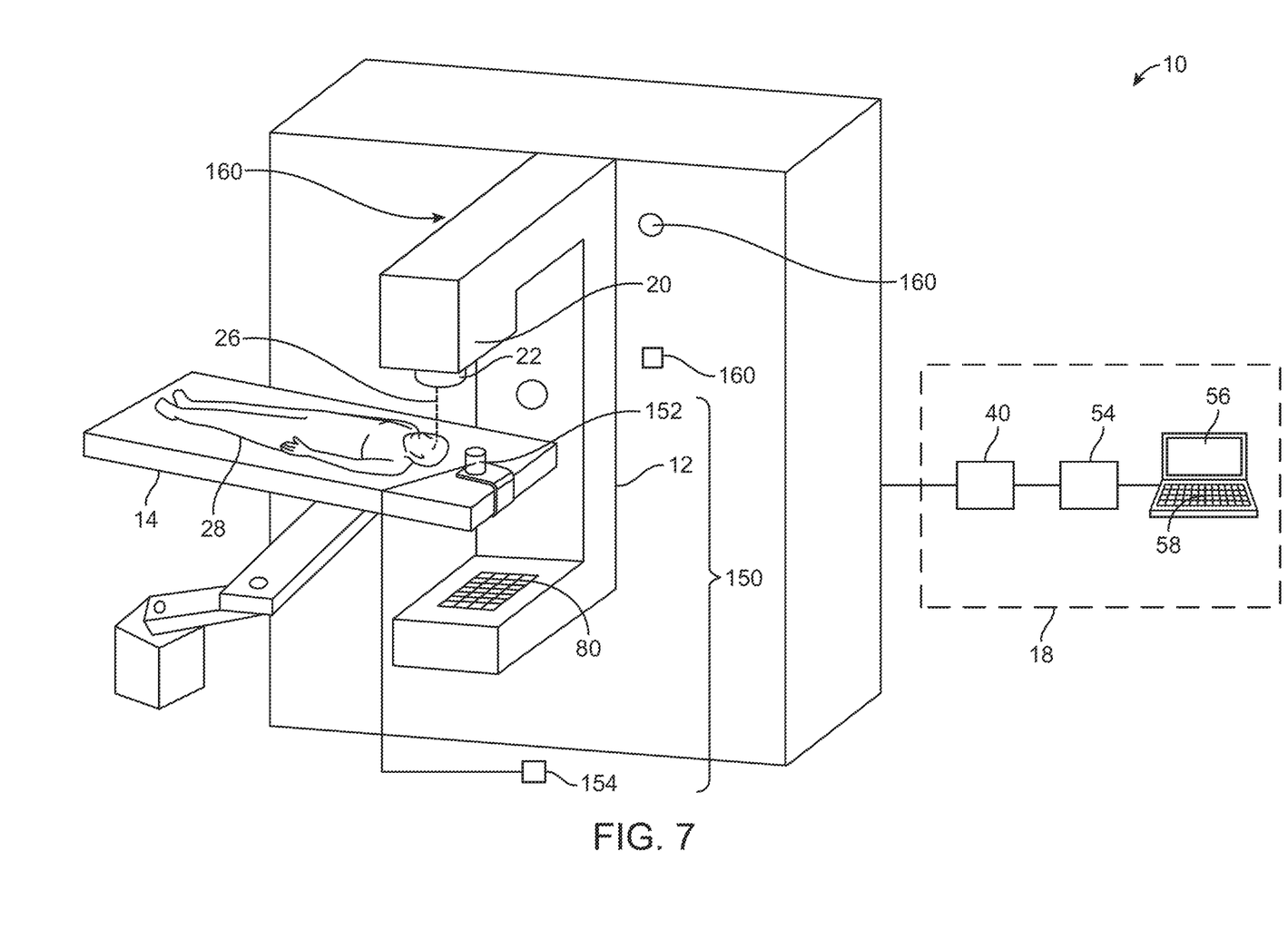
FIG. 7 illustrates a treatment system that includes a camera for attachment to a patient support.

In the above embodiments, the camera 152 is described with reference to it being attached to the patient 28. In other embodiments, the camera 152 may be attached to the patient support 14. FIG. 7 illustrates a treatment system 10 that includes the camera 152 for attachment to the patient support 14. During use, the camera 152 attached to the patient support 14 captures images of the environment next to the patient support 14. In some cases, such arrangement may allow the processing unit to monitor the position of the patient support 14 (e.g., to detect bending of the patient support 14, such as that caused by a heavy patient).

During use, the camera 152 is attached to the patient support 14. Also, one or more markers are attached to the system 10 or to a room. For example, the marker(s) may be attached to the floor of a room, while the camera 152 is attached to the patient support 14 (e.g., at the bottom of the patient support 14) and is oriented to view downward towards the marker(s). As another example, the marker(s) may be attached to wall(s) of the room, while the camera 152 is attached to the patient support 14 (e.g., at a side of the patient support 14) and is oriented to view the marker(s) on the wall(s). In some embodiments, there are three markers 160 attached to different parts of the system 10 or the room. As shown in the figure, the markers 160 are attached to different parts of a housing of the system 10. In other embodiments, the markers 160 may be attached to other components of the system 10. Each marker 160 may comprise a sticker for attachment to the system 10. The camera 152 is then used to capture images of the markers 160 for the purpose of position monitoring. In some embodiments, each marker 160 may have a geometric pattern for allowing the processing unit 154 processing the input image from the camera 152 to identify the marker 160. For example, a marker 160 may have a triangular shape, an elliptical shape, a circular shape, a square shape, or any of other shapes. In other embodiments, instead of being attached to the system 10, one or more of the markers 160 may be attached to a room (e.g., a ceiling, a wall, a floor, etc.). In some cases, the markers 160 may be part of an apparatus that also includes the camera 152 and the processing unit 154.

Figure 8:
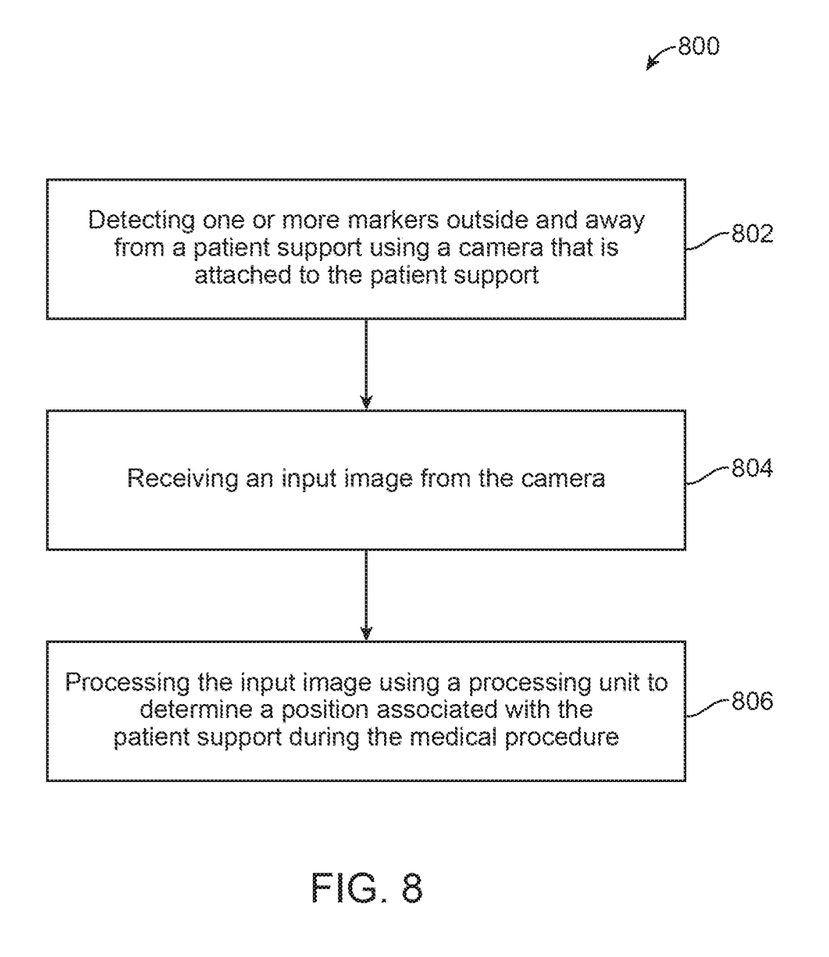
FIG. 8 illustrates a method of position monitoring.

FIG. 8 illustrates a method 800 of determining a position associated with a patient support during a medical procedure. First, one or more markers 160 outside and away from the patient support 14 are detected using the camera 152 that is attached to the patient support 14 (item 802). Next, an input image from the camera 152 is received by the processing unit 154 (item 804). Next, the input image is processed using the processing unit 154 to determine a position associated with the patient support 14 during the medical procedure (item 806).

In some embodiments, items 802, 804, 806 are repeated during the medical procedure in order to continuously track the position associated with the patient support 14. For example, the camera 152 may be configured to repeatedly generate real-time input images, and the processing unit 154 processes these input images in real-time (e.g., within a short time after the image is generated, such as within 1 second, and more preferably within 0.5 second, and more preferably within 0.1 second) to track the position associated with the patient support 14.

In the method 800, the processing unit 154 may be configured to perform the same functions as those described with reference to the method 300, except that the position being monitored is the position of the patient support 14 (instead of the position of the target associated with the patient 28).

For example, the processing unit 154 may be configured to determine a position of the patient support 14 based on an input image from the camera 152. In one implementation, the processing unit 154 may include a position determination module configured to calculate a position of the patient support 14 based on a pattern of the images of the markers 160 as they appear in an input image. The position determination module may calculate the position using triangulation technique and geometric principles. In some embodiments, the above process may be repeated to determine the position of the patient support 14 in real time while the medical procedure is being performed.

It should be noted that the position monitoring system 150 and methods 300, 800 described herein are not limited to application with medical systems that provide x-ray beams, and that the position monitoring system 150 and the methods 300, 800 may be employed in other types of medical system and procedures. For example, in other embodiments, the system 10 may be configured to provide proton beam. Also, as used in this specification, the term "radiation" may include "proton beam".

In addition, in any of the embodiments described herein, the position monitoring system 150 may include multiple cameras 152. For example, there may be multiple cameras 152 attached to a part of the patient 28, or to the patient support 14, for providing different fields of view of the markers 160.

Also, it should be noted that as used in this specification, the term "image" is not limited to an image that is displayed, and may refer to an image that is not displayed (e.g., an image in data or digital form that is stored).

Specialized Processing System

Figure 9:
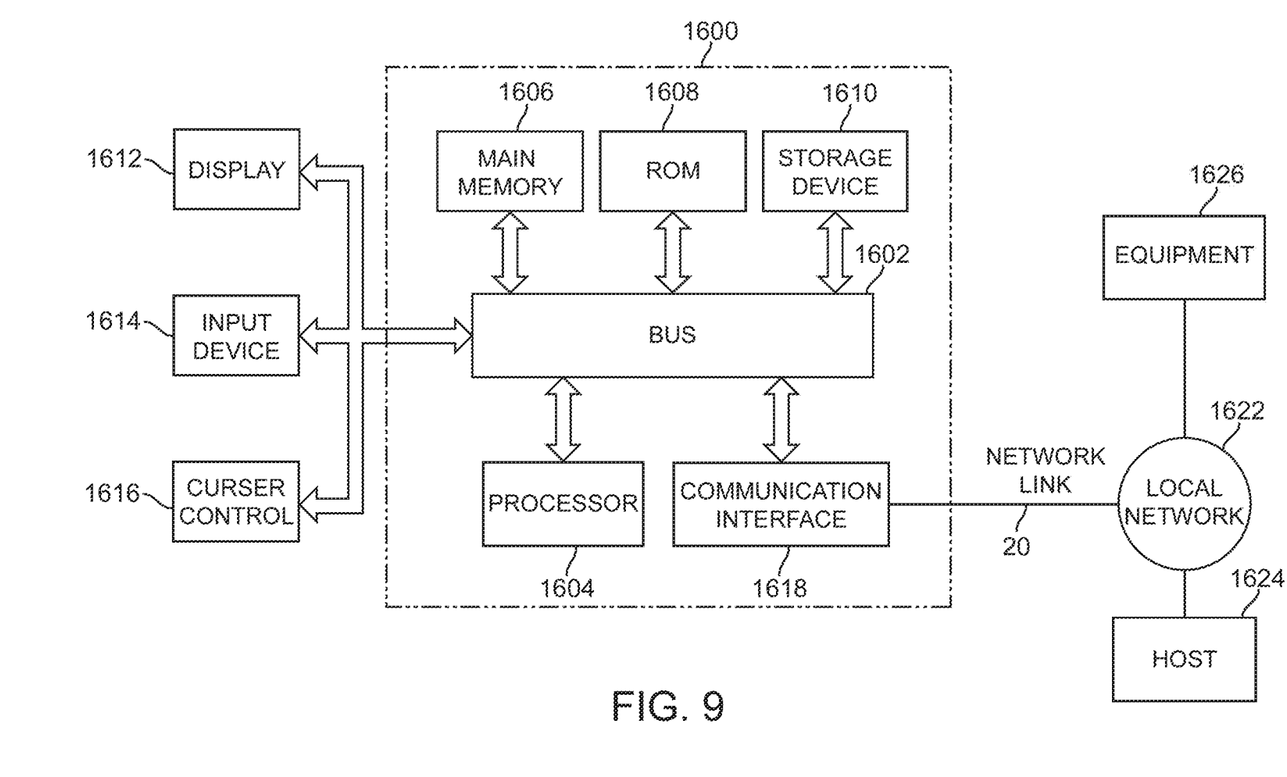
FIG. 9 is a diagram of a processing system with which embodiments described herein may be implemented.

FIG. 9 is a block diagram illustrating an embodiment of a specialized processing system 1600 that can be used to implement various embodiments described herein. For example, the processing system 1600 may be configured to perform the method 300 of FIG. 3 and/or the method 800 of FIG. 8. The processing system 1600 may also be an example of the processing unit 154. The processing system 1600 may also be any processor described herein. Also, in some embodiments, the processing system 1600 may be configured to process real-time input images from the camera 152 by comparing them with reference image (or reference template(s) derived therefrom) to monitor a position of a patient or a position of a patient support.

Referring to FIG. 9, the processing system 1600 includes a bus 1602 or other communication mechanism for communicating information, and a processor 1604 coupled with the bus 1602 for processing information. The processor system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processor system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The processor system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processor system 1600 can be used to perform various functions described herein. According to some embodiments, such use is provided by processor system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the processing system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

What is claimed:

1. An apparatus for use in a radiation treatment, comprising: a camera configured for attachment to a patient, and is configured to detect one or more markers outside and away from the patient; and a processing unit configured to be communicatively coupled with a component of a radiation delivery system, the processing unit also configured to receive an input image from the camera, and to process the input image during the radiation treatment to monitor a position of a target based on the one or more markers detected by the camera when the camera is attached to the patient.

2. The apparatus of claim 1, further comprising a connector for detachably connecting the camera to the patient.

3. The apparatus of claim 1, further comprising a structure for carrying the camera, wherein the processing unit is mounted to the structure.

4. The apparatus of claim 1, further comprising a structure for carrying the camera, wherein the processing unit is separate from the structure.

5. The apparatus of claim 1, further comprising a non-transitory medium for storing the input image and/or a reference image for comparison with the input image.

6. The apparatus of claim 1, wherein the processing unit is configured to receive a reference image from the camera, wherein the reference image or a reference template is for comparison with later acquired input images from the camera, wherein one of the later acquired input images is the input image.

7. The apparatus of claim 6, wherein the processing unit is further configured to obtain the reference template from processing the reference image.

8. The apparatus of claim 1, further comprising a headworn device, wherein the camera is coupled to the headworn device.

9. The apparatus of claim 8, wherein the headworn device comprises a pair of glasses, a goggle, a helmet, a face-mask, or a headphone.

10. The apparatus of claim 1, wherein the processing unit is configured to receive a reference image, extract multiple reference templates from the reference image, and match the reference templates with different parts of the input image.

11. The apparatus of claim 10, wherein the processing unit is further configured to determine multiple matched positions for the respective reference templates, and compare a pattern of the matched positions with a reference pattern.

12. The apparatus of claim 11, wherein the processing unit is configured to determine whether the patient has moved based on the comparison of the pattern with the reference pattern.

13. The apparatus of claim 1, further comprising the one or more markers.

14. The apparatus of claim 13, wherein one of the one or more markers is mounted at a housing of a treatment machine.

15. The apparatus of claim 13, wherein one of the one or more markers is mounted to a housing of an imaging machine.

16. The apparatus of claim 13, wherein one of the one or more markers is mounted to a room.

17. The apparatus of claim 13, wherein one of the one or more markers comprises a sticker having a geometric pattern.

18. The apparatus of claim 1, wherein the processing unit is configured to compare the input image with a reference image.

19. The apparatus of claim 18, wherein the processing unit is configured to compare the input image with the reference image by determining a correlation value representing a degree of two-dimensional correlation between the input image and the reference image.

20. The apparatus of claim 18, wherein the processing unit is configured to compare the input image with the reference image by performing cross-correlation.

21. The apparatus of claim 18, wherein the processing unit is further configured to generate a signal to stop a delivery of an energy beam if a result of the comparison indicates that the patient has moved.

22. The apparatus of claim 18, wherein the processing unit is further configured to generate one or more control signal(s) to move one or more corresponding components of a medical system if a result of the comparison indicates that the patient has moved.

23. The apparatus of claim 18, wherein the processing unit is configured to compare the input image with the reference image by performing an image subtraction between the input image and the reference image to obtain a subtracted image.

24. The apparatus of claim 23, wherein the processing unit is configured to calculate a metric based on an absolute difference of pixel values within a region of interest in a field of view of the camera that corresponds with one of the one or more markers.

25. The apparatus of claim 24, wherein the metric comprises a variance.

26. A method of monitoring a patient during a radiation treatment procedure that involves delivery of treatment radiation by a treatment radiation system, comprising: detecting one or more markers outside and away from a patient using a camera, the camera being a patient-mounted camera that is attached to the patient; receiving an input image from the camera; and processing the input image using a processing unit during the radiation treatment procedure to monitor a position of a target based on the one or more markers detected by the patient-mounted camera during the radiation treatment procedure, wherein the processing unit is configured to be communicatively coupled with a component of the treatment radiation system.

* * * * *